(12) United States Patent
St. George et al.

(10) Patent No.: US 10,349,961 B2
(45) Date of Patent: Jul. 16, 2019

(54) RETRACTION FORCE SENSING BASKET

(71) Applicant: Gyrus ACMI, Inc., Southborough, MA (US)

(72) Inventors: Lawrence J. St. George, Sudbury, MA (US); Artemie G. Gavala, Sutton, MA (US)

(73) Assignee: Gyrus ACMI, Inc., Southborough, MA (US)

( * ) Notice: Subject to any disclaimer, the term of this patent is extended or adjusted under 35 U.S.C. 154(b) by 204 days.

(21) Appl. No.: 15/646,479

(22) Filed: Jul. 11, 2017

(65) Prior Publication Data

US 2017/0303945 A1    Oct. 26, 2017

Related U.S. Application Data

(62) Division of application No. 15/156,715, filed on May 17, 2016, now Pat. No. 9,724,115.
(Continued)

(51) Int. Cl.
*A61B 17/221*    (2006.01)
*A61B 90/00*    (2016.01)
(Continued)

(52) U.S. Cl.
CPC ............ *A61B 17/221* (2013.01); *A61B 90/03* (2016.02); *A61B 17/22031* (2013.01);
(Continued)

(58) Field of Classification Search
CPC ................. A61B 90/03; A61B 17/221; A61B 2017/00119; A61B 2017/00128; A61B 2090/034; A61B 17/2909; A61B 17/32056; A61B 17/2833; A61B 17/22031; A61B 2017/2837; A61B 2017/291; A61B 2090/064; A61B 2090/0807; A61B 2017/2924; A61B 2017/00407; A61B 2017/00455; A61B 2017/2923; A61B 2017/2212
See application file for complete search history.

(56) References Cited

U.S. PATENT DOCUMENTS 5,084,054 A *  1/1992  Bencini .............. A61B 17/2909
                                                    606/113
5,944,728 A *  8/1999  Bates ................... A61B 17/221
                                                    604/264
(Continued)

*Primary Examiner* — Phong Son H Dang
(74) *Attorney, Agent, or Firm* — Yi Chen

(57) ABSTRACT

A stone retrieval device includes a sheath and a stone retrieval basket that includes a distal region with a plurality of basket wires and a proximal region with one or more core wires. The stone retrieval basket is contained within the sheath and is movable out a distal opening of the sheath to cause the plurality of basket wires to open into a basket shape. The stone retrieval device further includes a lock mechanism that locks the position of the stone retrieval basket with respect to the position of the sheath and a basket force controller that includes a first and a second control stage. The first control stage includes a sensor for measuring force on the stone retrieval basket when the lock mechanism is in an unlocked position, and the second control stage includes a sensor for measuring force when the lock mechanism is in a locked position.

8 Claims, 4 Drawing Sheets

Related U.S. Application Data

(60) Provisional application No. 62/184,623, filed on Jun. 25, 2015.

(51) Int. Cl.
*A61B 17/00* (2006.01)
*A61B 17/29* (2006.01)
*A61B 17/28* (2006.01)
*A61B 17/22* (2006.01)
*A61B 17/3205* (2006.01)

(52) U.S. Cl.
CPC ....... *A61B 17/2833* (2013.01); *A61B 17/2909* (2013.01); *A61B 17/32056* (2013.01); *A61B 2017/00119* (2013.01); *A61B 2017/00128* (2013.01); *A61B 2017/00407* (2013.01); *A61B 2017/00455* (2013.01); *A61B 2017/2212* (2013.01); *A61B 2017/2837* (2013.01); *A61B 2017/291* (2013.01); *A61B 2017/2923* (2013.01); *A61B 2017/2924* (2013.01); *A61B 2090/034* (2016.02); *A61B 2090/064* (2016.02); *A61B 2090/0807* (2016.02)

(56) References Cited

U.S. PATENT DOCUMENTS

| | | | | |
|---|---|---|---|---|
| 5,957,932 A * | 9/1999 | Bates | ................... | A61B 17/221 606/113 |
| 6,096,053 A * | 8/2000 | Bates | ................... | A61B 17/221 606/159 |
| 2002/0091394 A1 * | 7/2002 | Reynolds | ......... | A61B 17/00234 606/127 |
| 2003/0144672 A1 * | 7/2003 | Gellman | ............... | A61B 17/221 606/127 |
| 2004/0122445 A1 * | 6/2004 | Butler | ............... | A61B 17/22031 606/127 |
| 2004/0176672 A1 * | 9/2004 | Silver | .................. | A61B 5/0031 600/345 |
| 2004/0199200 A1 * | 10/2004 | Teague | .................. | A61B 17/221 606/200 |
| 2005/0261705 A1 * | 11/2005 | Gist | ..................... | A61B 17/221 606/113 |
| 2008/0009884 A1 * | 1/2008 | Kennedy, II | ......... | A61B 17/221 606/127 |
| 2009/0030427 A1 * | 1/2009 | Razvi | ................. | A61B 17/22031 606/127 |
| 2011/0118746 A1 * | 5/2011 | Fischer | ................ | A61B 17/221 606/128 |
| 2012/0065660 A1 * | 3/2012 | Ferrera | ..................... | A61F 2/01 606/198 |
| 2013/0345739 A1 * | 12/2013 | Brady | .................. | A61B 17/221 606/200 |
| 2014/0343585 A1 * | 11/2014 | Ferrera | ................ | A61B 17/221 606/159 |
| 2014/0364926 A1 * | 12/2014 | Nguyen | .................. | A61F 7/007 607/99 |
| 2017/0150979 A1 * | 6/2017 | Ulm, III | ............. | A61B 17/221 |
| 2017/0172591 A1 * | 6/2017 | Ulm, III | ........... | A61B 17/12109 |

* cited by examiner

RETRACTION FORCE SENSING BASKET

RELATED APPLICATION

The present application is a divisional of Ser. No. 15/156,715, filed on May 17, 2016, which claims priority to U.S. Provisional Application No. 62/184,623, filed on Jun. 25, 2015; the entire contents of each of these applications are hereby incorporated by reference.

FIELD

The present disclosure relates to a medical device. More specifically, the present disclosure relates to a medical device for capturing one or more stone fragments.

BACKGROUND

The statements in this section merely provide background information related to the present disclosure and may or may not constitute prior art.

During ureteroscopy or percutaneous nephrolithotomy (PCNL) procedures, baskets are often employed to capture and retrieve stone fragments from a patient's anatomy. After the stone fragments have been removed from the patient and released from the basket, the basket is re-inserted one or more times into the patient's anatomy to remove all or most of the remaining stone fragments. In some instances, however, stone fragments that are too large are captured in the basket, which may result in the basket getting stuck in the ureter or access sheath. If the basket can be pushed back, some fragments can be released and the basket can then be pulled out of the patient. If the basket is completely stuck, the basket can be cut apart from the basket handle and sheath, or a small laser fiber may be inserted into the patient so that laser ablation can be utilized to break up the stone fragments. In any case, if the basket damaged, a new basket has to be employed to complete the medical procedure, which may increase the surgical time and costs.

Among the literature that can pertain to this technology include the following patent documents and published patent applications: U.S. Pat. Nos. 7,645,283, 5,944,728, US 2005/0261705, and DE69828984, the entire contents of which are incorporated herein by reference for all purposes.

Accordingly, to reduce surgical cost and time, there is a need for a stone retrieval device that prevents the basket from getting stuck in the ureter to minimize trauma to the ureter during retrieval of stone fragments.

SUMMARY

The present invention provides an improved medical device for capturing one or more stone fragments and a method of using such a device.

In one aspect, a stone retrieval device includes a sheath and a stone retrieval basket that includes a distal region with a plurality of basket wires and a proximal region with one or more core wires. The stone retrieval basket is contained within the sheath and is movable out a distal opening of the sheath to cause the plurality of basket wires to open into a basket shape. The stone retrieval device further includes a lock mechanism that locks the position of the stone retrieval basket with respect to the position of the sheath and a basket force controller that includes a first control stage and a second control stage. The first control stage includes a sensor for measuring force on the stone retrieval basket when the lock mechanism is in an unlocked position, and the second control stage includes a sensor for measuring force on the stone retrieval basket when the lock mechanism is in a locked position.

The stone retrieval device may be further characterized by one or any combination of the features described herein, such as, for example: the lock mechanism is a ratchet mechanism; the ratchet mechanism includes a first protrusion associated with a first member and a set of notches associated with a second member, the first member being contained in the second member and movable relative to the second member, the first protrusion being engaged with one notch of the set of notches when the lock mechanism is in the locked position; the one or more core wires is attached to a third member contained in the first member, the third member being movable relative to the first member and including a second protrusion, the second protrusion being engaged with the first protrusion when the lock mechanism is in the locked position; movement of the third member relative to the first member pulls the plurality of basket wires into the distal opening of the sheath; the first control stage sensor is a visual indicator with a first color; the second control stage sensor is a visual indicator with a second color that is different than the first color; at least one of the sensors of the first control stage and the second control stage is a pop-up flag; at least one of the sensors of the first control stage and the second control stage is a tactile sensor; at least one of the sensors of the first control stage and the second control stage is a sonic sensor; the stone retrieval device further includes an automatic release mechanism that releases the stone retrieval basket when the force on the stone retrieval basket exceeds a predetermined maximum force; and the automatic release mechanism is resettable after releasing the stone retrieval basket.

In another aspect, the present disclosure provides a method of determining a force on a stone retrieval basket including one or more of the following steps: capturing a stone with the stone retrieval basket; and utilizing a sensor to determine if the force on the stone retrieval basket exceeds a predetermined maximum force. The method may be further characterized by one or any combination of the features described herein, such as, for example: the sensor is visual sensor; and the method further includes releasing the stone retrieval basket when the force on the stone retrieval basket exceeds the predetermined maximum force.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, emphasis instead being placed upon illustrating the principles of the invention. Moreover, in the figures, like reference numerals designate corresponding parts throughout the views. In the drawings.

DETAILED DESCRIPTION

The following description is merely exemplary in nature and is not intended to limit the present disclosure, application, or uses.

Figure 1:
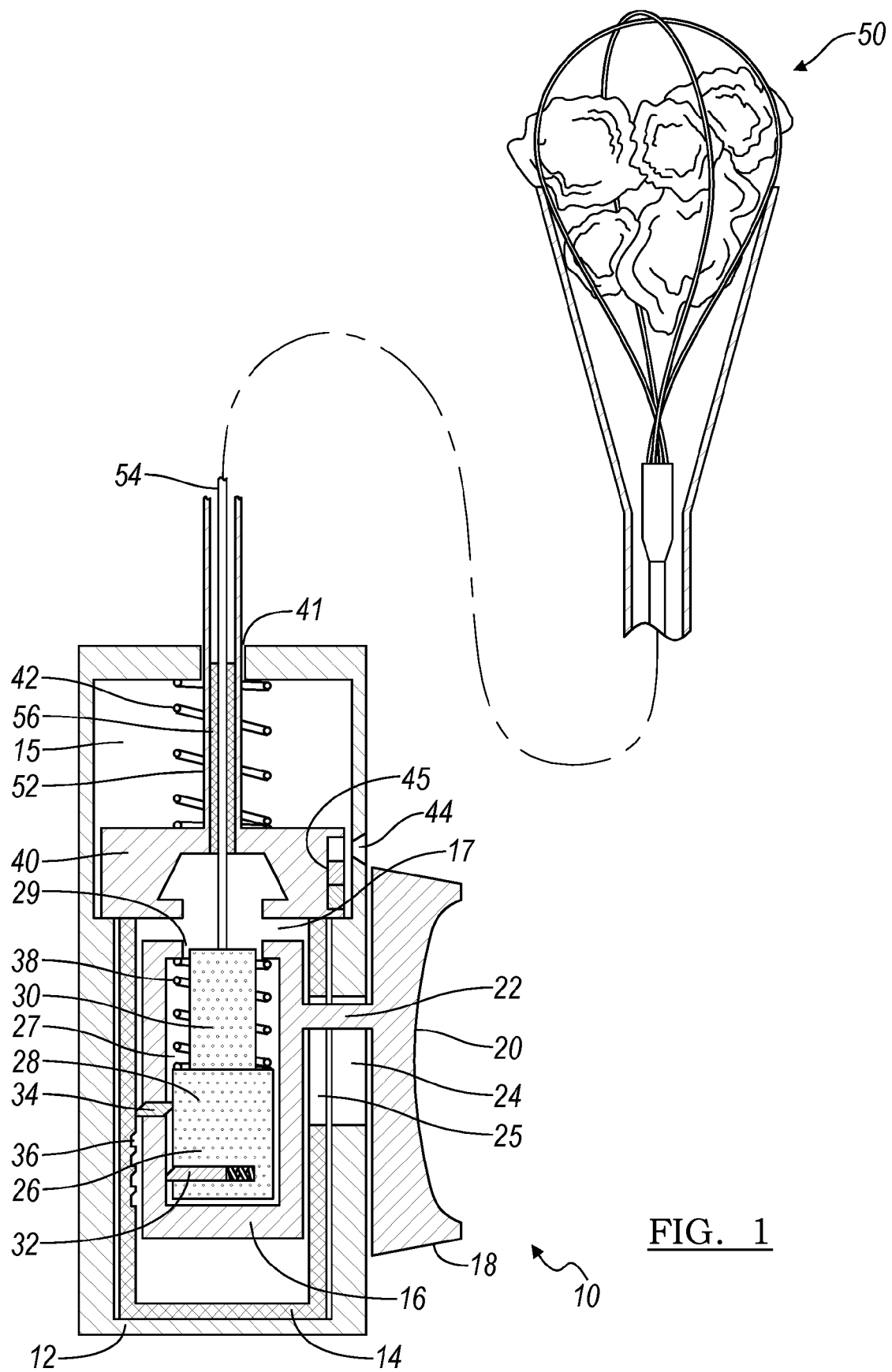
FIG. 1 is side cross-sectional view of a stone retrieval device in accordance with the principles of the present invention.
Figure 2:
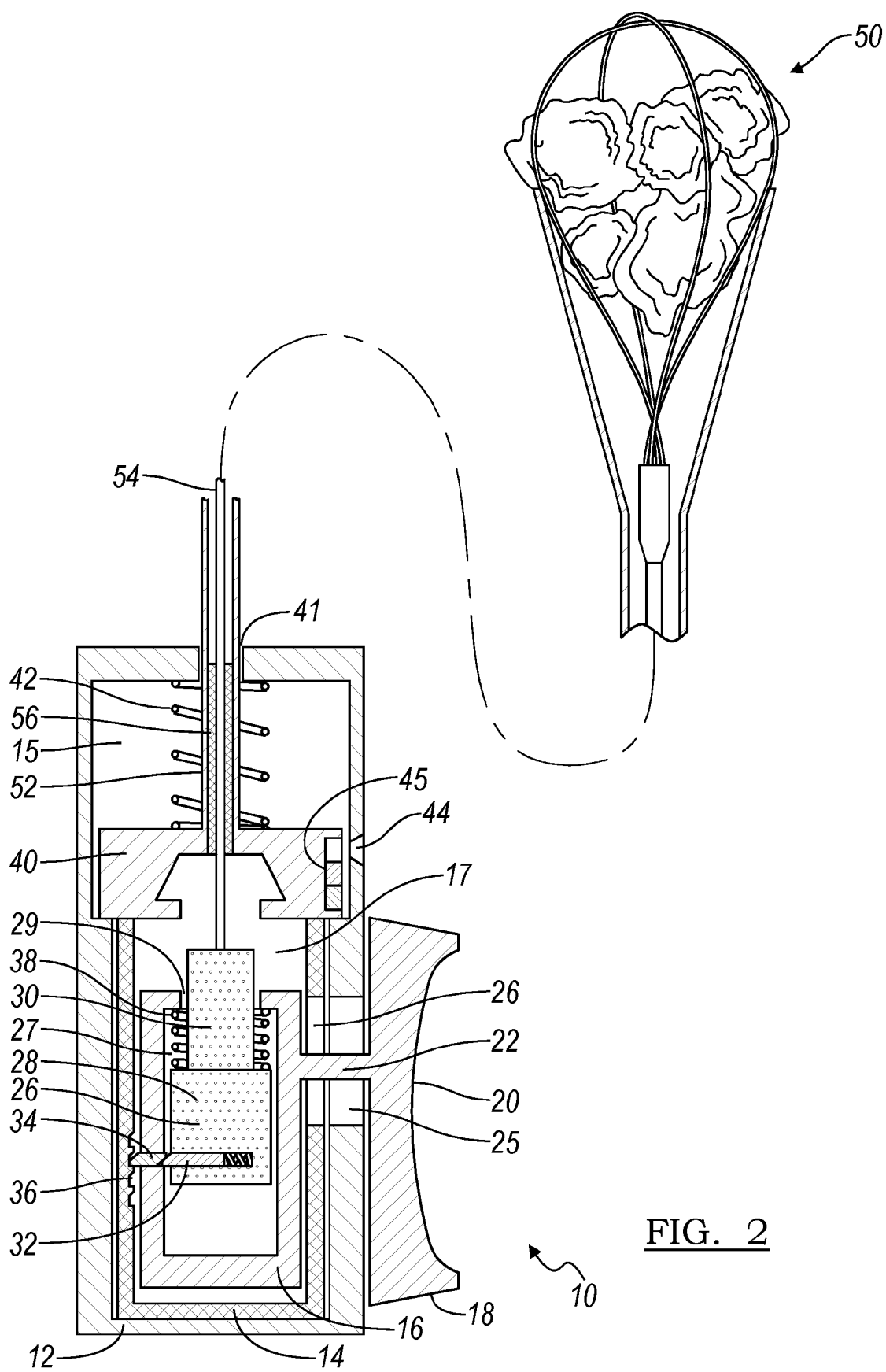
FIG. 2 is a side cross-sectional view of the stone retrieval device shown in FIG. 1 when the device is in a locked position.
Figure 3:
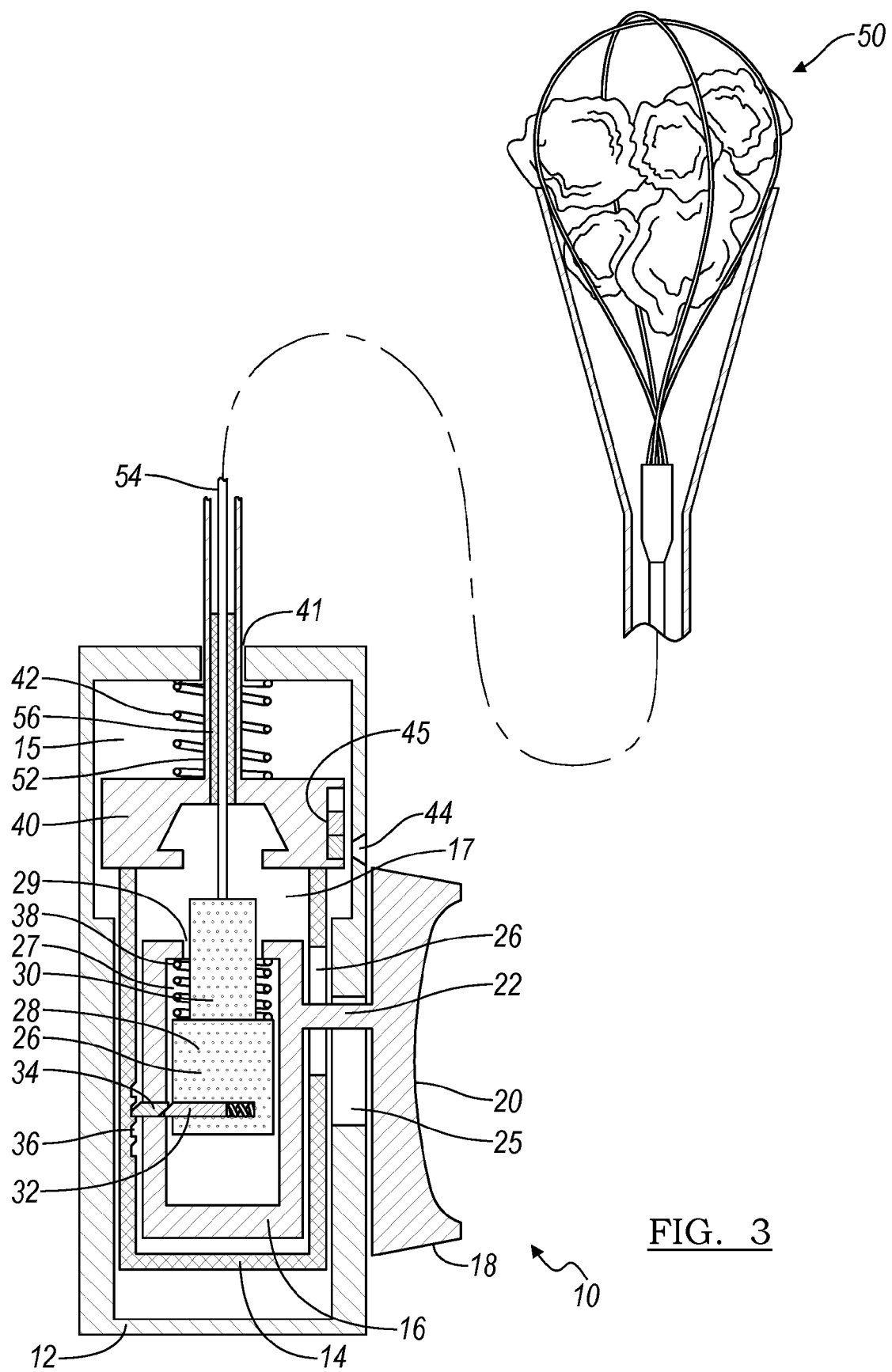
FIG. 3 is a side cross-sectional view of the stone retrieval device shown in FIG. 1 when the device is applying a maximum pull force on one or more stone fragments.

Referring now to the drawings, a stone retrieval device embodying the principles of the present invention is illustrated in FIGS. 1 through 3 and designated at 10. The stone retrieval device 10 includes a housing 12, a first member 14 contained within a space 15 of the housing 12, a second member 16 contained within a space 17 the first member 14, and a third member 26 contained within a space 27 the second member 16. The third member 26 includes an enlarged portion 28 and a smaller portion 30.

The third member 26 is able to slide back and forth within the second member 16, and a protrusion 32 embedded in the enlarged portion 28 selective engages with a protrusion 34 embedded in the second member 16. A biasing member 38, such as, for example, a coiled spring, is positioned about the smaller portion 30. The biasing member 38 is arranged to urge the third member 26 away from an opening 29 of the second member 16.

The second member 16 is arranged to slide back and forth within the space 17 of the first member 14. The protrusion 34 extends outwardly from the second member 16 such that the protrusion 34 selectively engages with a notch of a set of notches 36 located on an inner surface of the first member 14. Hence, engagement of the protrusion 32 with the protrusion 34 and engagement of the protrusion 34 with one of the notches of the set of notches 36 operates as a ratchet or locking mechanism to lock the position of the third member 26 and the second member 16 relative to the first member 14 in a locked position. When the protrusion 34 is unengaged with any of the notches of the set of notches 36. The second member 16, and consequently, the third member 26, are in an unlocked position relative to the first member 14.

A positioner 18 includes an extension 22 that extends through an opening 24 of the housing 12 and an opening 25 of the first member 14. The extension 22 is attached to the second member 16. An operator of the stone retrieval device 10, such as a physician, can therefore place, for example, a thumb on an indentation 20 of the positioner 18 and push or pull on the positioner 18 to move the second member 16 relative to the first member 14 and the housing 12.

In certain arrangements, the stone retrieval device 10 includes a sensor such as, for example, a pull-force sensor with an opening 44 associated with the housing 12 and a set of color indicators 45 embedded in an enlarged portion 40 of the first member 14 that the operator can view through the opening 44. Accordingly, as the first member 14 slides within the space 15 of the housing 12. Different colored indicators of the set of indicators 45 are observed through the opening 44. Another biasing member such as, for example, a coiled spring 42 is positioned about an extension 56 that extends from the enlarged portion 40 of the first member 14. The biasing member 42 is arranged to urge the first member 14 away from an opening 41 of the housing 12.

Figure 4:
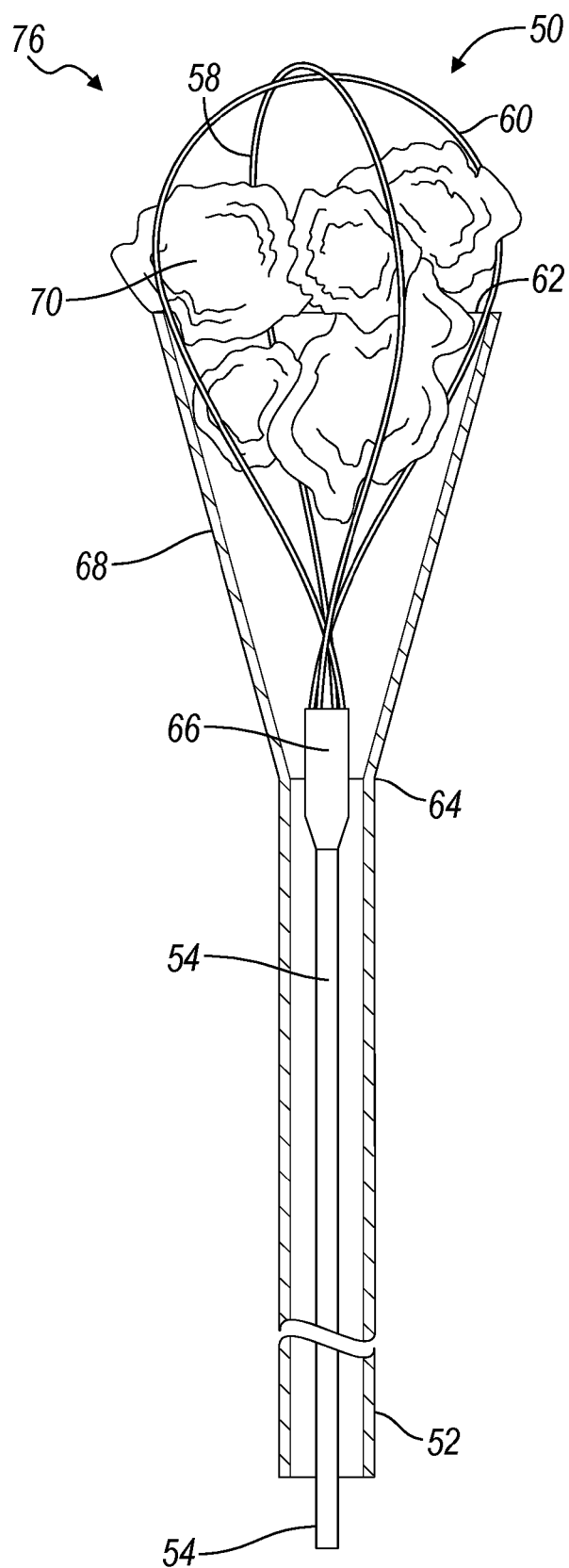
FIG. 4 is a partial cross-sectional view of a basket device employed with the stone retrieval device shown in FIG. 1 in accordance with the principles of the present invention.

In various arrangements, the stone retrieval device is attached or connected to a capturing device 50, which is shown in greater detail in FIG. 4. The capturing device 50, further a capturing basket 76, is positioned within the sheath 52 and an optional expandable cone 68. The capturing basket 76 includes a rod or wire 54 with a distal end 66 and a proximal end 67 attached to the smaller portion 30 of the first member 26. A pair of wires 58 and 60 are attached to the distal end 66 of the rod or wire 54. Specifically, the ends of each of the wires 58 and 60 are attached to the distal end 66 such that the mid region of the wires 58 and 60 intersect at the distal most end of the capturing basket 76. As shown in FIG. 4, the wires 58 and 60 are generally orthogonal to each other at the distal point of intersection for this particular arrangement. In addition to surrounding the rod or wire 54, the proximal region of the sheath 52 extends through the opening 41 of the housing 12, surrounds the extension 56 and is positioned within the coiled spring 42. The sheath 52 is attached or connected to the enlarged portion 40 of the first member 14. Thus, movement of the third member 26 relative to the first member 14 results in movement of the rod or wire 54 relative to the sheath 52. Different color indicators of the set of color indicators 45 viewed through the opening 44 indicates the pull force on the capturing basket 76. Rather than color indicators, the pull-force sensor can be a sonic sensor, a tactile sensor, a pop-up flag or any other suitable sensor that indicates the pull force on the capturing basket 76.

When the capturing device 50 includes the optional cone 68, the capturing basket 76 is initially collapsed within the cone 68 as the capturing device 50 is inserted into an anatomical region of a patient. After the capturing basket 76 and the cone 68 have been positioned in the anatomical region containing stone fragments, the operator of the stone retrieval device 10 pushes on the positioner 18 distally such that the wires 58 and 60 exit a distal end 62 of the expandable cone 68. After the stone fragments 70 have been captured by the wires 58 and 60, the operator pulls on the positioner 18 proximally to draw the stone fragments 70 into the cone 68, which causes the cone 68 to expand. The distal end 62 of the cone 68 is configured to expand to a maximum predetermined size.

As the operator of the stone retrieval device 10 pulls the positioner 18 distally, the second member 16 moves proximally relative to the first member 16 such that the protrusion 34 eventually engages with one of the notches of the set of notches 36 associated the first member 14. Further, the proximal movement of the second member 14 also results in movement of the second member 14 relative to the third ember 26. Such movement results in engagement of the protrusion 34 with the protrusion 32 embedded in the third member 26 and compression of the coiled spring 38. As described earlier, engagement of the protrusion 34 with the protrusion 36 and with one of the notches of the set of notches 36 locks the third member 26 and the second member 16 with the first member 14 in a locked position (FIG. 2). To unlock the members, the operator pushes on the position 18 such that the protrusion 34 becomes unlocked from the set of notches 36 and the coiled spring 38 pushes the third member 26 proximally relative to the second member 16 to unengaged the protrusion 34 from the protrusion 32.

During the stone removal procedure, the operator can view the color indicators 45 through the opening 44. A first color indicator, such as a light color, can indicate to the operator that the pull force on the stone fragments 70 with not trauma or damage to the patient's ureter. As the operator pulls on the housing 12 when the stone retrieval device is in the locked positions, the operator continues to view the color indicators 45 through the opening 44. Additional pull force moves the first member 14 distally relative to the housing 12, resulting in compression of the coiled spring 42 and movement of the set of color indicators 45 relative to the opening 44. A second color indicator, such as a darker color, may serve as a warning to the operator that the pull force on the stone fragments is approaching a maximum limit. A third color indicator, such as a darkest color of the set of color indicators, may indicate to the operator that the pulls force is at the maximum limit and any additional pull force may damage the patient's ureter. Reducing the pull force results in the coiled spring 42 pushing the first member proximally relative to the housing 12 such that the lighter colored indicators of the set of indicators 45 are viewed through the opening 44 to indicate to the operator that the pull force on the capturing basket 76 has been reduced to a desired level.

The description of the invention is merely exemplary in nature and variations that do not depart from the gist of the invention are intended to be within the scope of the invention. Such variations are not to be regarded as a departure from the spirit and scope of the invention.

What is claimed is:

1. A method of determining a force on a stone retrieval basket comprising:
    capturing a stone with the stone retrieval basket;
    measuring the force on the stone retrieval basket with a force sensor; and providing an indication to a user of the stone retrieval basket to
    determining if the force on the stone retrieval basket exceeds a predetermined maximum force, wherein the indication is one of visual, pop-up flag, tactile or sonic.

2. The method of claim 1, further comprising releasing the stone retrieval basket if the force on the stone retrieval basket exceeds the predetermined maximum force.

3. The method of claim 1, wherein capturing the stone comprises engaging a locking mechanism.

4. The method of claim 3, wherein engaging the locking mechanism includes engaging a ratchet mechanism.

5. The method of claim 4, wherein the ratchet mechanism includes a first protrusion associated with a first member and a set of notches associated with a second member, the first member being contained in the second member and movable relative to the second member, the first protrusion being engaged with one notch of the set of notches when the locking mechanism is in a locked position.

6. The method of claim 5, wherein the stone retrieval basket includes a distal region with a plurality of basket wires and a proximal region with one or more core wires, the stone retrieval basket being contained within a sheath and movable out of a distal opening of the sheath to cause the plurality of basket wires to open into a basket shape.

7. The method of claim 6, further comprises engaging the one or more core wires attached to a third member contained in the first member, the third member being movable relative to the first member and including a second protrusion, the second protrusion being engaged with the first protrusion when the locking mechanism is in the locked position.

8. The method of claim 7, wherein moving the third member relative to the first member pulls the plurality of basket wires into the distal opening of the sheath.

* * * * *